US010918763B2

(12) United States Patent
Zhu et al.

(10) Patent No.: US 10,918,763 B2
(45) Date of Patent: Feb. 16, 2021

(54) COMBINED FULLY ORGANIC HIGH MOLECULAR MATERIAL ARTIFICIAL KNEE JOINT

(71) Applicant: JIANGSU OKANI MEDICAL TECHNOLOGY CO., LTD, Taicang (CN)

(72) Inventors: Jack Zhu, Taicang (CN); Longwei Xu, Taicang (CN)

(73) Assignee: JIANGSU OKANI MEDICAL TECHNOLOGY CO., LTD, Taicang (CN)

(*) Notice: Subject to any disclaimer, the term of this patent is extended or adjusted under 35 U.S.C. 154(b) by 0 days.

(21) Appl. No.: 15/550,357

(22) PCT Filed: Sep. 25, 2015

(86) PCT No.: PCT/CN2015/000664
§ 371 (c)(1),
(2) Date: Aug. 10, 2017

(87) PCT Pub. No.: WO2016/127282
PCT Pub. Date: Aug. 18, 2016

(65) Prior Publication Data
US 2018/0028718 A1 Feb. 1, 2018

(30) Foreign Application Priority Data
Feb. 10, 2015 (CN) .......................... 2015 1 0070528

(51) Int. Cl.
*A61F 2/38* (2006.01)
*A61L 27/16* (2006.01)
(Continued)

(52) U.S. Cl.
CPC ................. *A61L 27/16* (2013.01); *A61F 2/38* (2013.01); *A61F 2/3859* (2013.01);
(Continued)

(58) Field of Classification Search
CPC ........ A61F 2/38; A61F 2/3859; A61F 2/3868; A61F 2002/3863; A61F 2/3872; A61F 2/389
See application file for complete search history.

(56) References Cited

U.S. PATENT DOCUMENTS 4,938,774 A 7/1990 Tepic
5,021,061 A * 6/1991 Wevers ..................... A61F 2/38
623/20.18
(Continued)

FOREIGN PATENT DOCUMENTS

CN 101904777 A 8/2010
CN 201899585 A 7/2011
(Continued)

OTHER PUBLICATIONS

Translated Written Opinion of the International Search Authority issued to PCT Application No. PCT/CN2015/000664 dated Dec. 18, 2015.
(Continued)

*Primary Examiner* — Alvin J Stewart
(74) *Attorney, Agent, or Firm* — Hackler Daghighian Martino & Novak

(57) ABSTRACT

A combined fully organic high molecular material artificial knee joint, comprising a femur condyle (2), a tibia holder (4) and a tibia liner (3), the femur condyle (2) and the tibia holder (4) being formed by polyether ether ketone (PEEK) or derivatives thereof, and the tibia liner (3) being formed by ultra-high molecular weight polyethylene (UHMWPE). The tibia holder (4) comprises a platform (6) and a stable wing positioning portion (5) vertical thereto; upper and lower ends of the tibia liner (3) are jointed with the femur condyle (2) and the platform (6) respectively; the femur condyle (2) buffers a slide surface of the tibia liner (3); and the tibia holder (4) can finely move relative to a fixed surface of the tibia liner (3), and buffering of the femur condyle (2) against the slide surface of the tibia liner (3) matches fine movement of the tibia holder (4) relative to the tibia liner (3). Main parts of all implant components of the artificial knee joint are formed by high molecular materials, thereby relieving allergy and toxicity problems probably caused by metal and (Continued)

metal corrosion; PEEK elastic modulus matches a natural bone, thereby relieving a stress shield problem; a wearing problem is greatly relieved by means of the combination of buffering of the PEEK femur condyle (2) against the slide surface of the UHMWPE tibia liner (3) and fine movement of the tibia holder (4) relative to the fixed surface of the UHMWPE tibia liner (3); and meanwhile, by adding enhancement and developing components, the practicality is further improved.

14 Claims, 3 Drawing Sheets

(51) Int. Cl.
  *A61L 27/04* (2006.01)
  *A61L 27/06* (2006.01)
  *A61L 27/18* (2006.01)

(52) U.S. Cl.
  CPC ............ *A61F 2/3868* (2013.01); *A61L 27/04* (2013.01); *A61L 27/06* (2013.01); *A61L 27/18* (2013.01); *A61F 2002/3863* (2013.01); *A61L 2430/24* (2013.01)

(56) References Cited

U.S. PATENT DOCUMENTS

| | | | |
|---|---|---|---|
| 5,171,282 A * | 12/1992 | Pequignot | A61F 2/30907 623/20.35 |
| 5,549,702 A | 8/1996 | Ries et al. | |
| 6,096,084 A | 8/2000 | Townley | |
| 6,214,051 B1 * | 4/2001 | Badorf | A61F 2/3859 623/20.14 |
| 6,383,222 B1 * | 5/2002 | Badorf | A61F 2/3877 623/20.21 |
| 6,503,281 B1 | 1/2003 | Mallory | |
| 7,833,274 B2 * | 11/2010 | Popoola | A61F 2/38 623/20.35 |
| 8,088,169 B2 | 1/2012 | Dorr et al. | |
| 8,252,062 B2 | 8/2012 | Bandoh et al. | |
| 8,333,805 B2 * | 12/2012 | Williams | A61L 27/306 623/20.35 |
| 8,834,573 B2 * | 9/2014 | Metzger | A61F 2/38 623/20.14 |
| 9,061,090 B2 | 6/2015 | Bandoh et al. | |
| 9,107,755 B2 * | 8/2015 | Popoola | A61F 2/38 |
| 9,119,722 B1 | 9/2015 | Kusuma | |
| 9,672,758 B2 * | 6/2017 | Sivadas | G09B 23/30 |
| 9,757,242 B2 * | 9/2017 | Dong | A61F 2/389 |
| 9,907,660 B2 | 3/2018 | Wang et al. | |
| 10,213,314 B2 | 2/2019 | Armacost et al. | |
| 10,646,348 B2 * | 5/2020 | Mitrovic | A61F 2/3859 |
| 10,667,920 B2 * | 6/2020 | Sedel | A61F 2/3886 |
| 2002/0065562 A1 | 5/2002 | Storer | |
| 2002/0072805 A1 | 6/2002 | Sullivan et al. | |
| 2003/0014123 A1 | 1/2003 | Copf et al. | |
| 2003/0163202 A1 | 8/2003 | Lakin | |
| 2004/0193276 A1 | 9/2004 | Maroney et al. | |
| 2005/0085915 A1 | 4/2005 | Steinberg | |
| 2005/0149198 A1 * | 7/2005 | Hawkins | A61F 2/389 623/20.14 |
| 2005/0203633 A1 | 9/2005 | Fernandes et al. | |
| 2005/0256585 A1 | 11/2005 | Park et al. | |
| 2005/0256586 A1 | 11/2005 | Kraus et al. | |
| 2006/0085079 A1 | 4/2006 | Carroll | |
| 2006/0184250 A1 | 8/2006 | Bandoh et al. | |
| 2006/0184251 A1 | 8/2006 | Zhang et al. | |
| 2006/0190086 A1 * | 8/2006 | Clemow | A61F 2/38 623/20.15 |
| 2007/0208428 A1 | 9/2007 | Tepic et al. | |
| 2007/0227024 A1 | 10/2007 | Beaule | |
| 2007/0270975 A1 | 11/2007 | Taylor et al. | |
| 2007/0276399 A1 | 11/2007 | Medley et al. | |
| 2008/0004710 A1 | 1/2008 | Ledger et al. | |
| 2008/0033577 A1 | 2/2008 | Kohan | |
| 2008/0200991 A1 | 8/2008 | Collins et al. | |
| 2008/0215483 A1 | 9/2008 | Grundei et al. | |
| 2008/0262626 A1 | 10/2008 | Raugel | |
| 2008/0288081 A1 * | 11/2008 | Scrafton | A61F 2/38 623/20.33 |
| 2009/0018666 A1 | 1/2009 | Grundei et al. | |
| 2009/0048681 A1 | 2/2009 | Vlachos | |
| 2009/0093887 A1 | 4/2009 | Walter et al. | |
| 2009/0149965 A1 | 6/2009 | Quaid | |
| 2009/0157191 A1 | 6/2009 | Collins et al. | |
| 2009/0192620 A1 | 7/2009 | Ebbitt | |
| 2009/0209963 A1 | 8/2009 | Jamali | |
| 2009/0248170 A1 | 10/2009 | Tuke et al. | |
| 2009/0306788 A1 | 12/2009 | Timoteo et al. | |
| 2010/0042225 A1 * | 2/2010 | Shur | A61F 2/38 623/20.35 |
| 2010/0049329 A1 | 2/2010 | Vio | |
| 2010/0076570 A1 | 3/2010 | Band et al. | |
| 2010/0094430 A1 | 4/2010 | Krumdieck | |
| 2010/0100190 A1 | 4/2010 | May | |
| 2010/0191341 A1 * | 7/2010 | Byrd | A61F 2/38 623/20.3 |
| 2010/0262144 A1 | 10/2010 | Kelman et al. | |
| 2010/0262250 A1 | 10/2010 | Kellar et al. | |
| 2010/0298944 A1 | 11/2010 | Bishop et al. | |
| 2010/0298949 A1 | 11/2010 | McMinn et al. | |
| 2010/0305713 A1 | 12/2010 | Grundei | |
| 2010/0312348 A1 | 12/2010 | Wang et al. | |
| 2011/0087333 A1 | 4/2011 | Kellar et al. | |
| 2011/0153025 A1 | 6/2011 | McMinn | |
| 2011/0264233 A1 | 10/2011 | Song | |
| 2011/0276143 A1 * | 11/2011 | He | A61L 27/16 623/18.11 |
| 2012/0029650 A1 | 2/2012 | Bruce | |
| 2012/0150315 A1 | 6/2012 | Forsell | |
| 2013/0006371 A1 * | 1/2013 | Wogoman | A61B 17/1764 623/20.21 |
| 2013/0006376 A1 * | 1/2013 | Wogoman | A61F 2/389 623/20.32 |
| 2013/0060347 A1 | 3/2013 | McMinn | |
| 2013/0345827 A1 | 12/2013 | Wallick | |
| 2014/0180424 A1 | 6/2014 | Dickerson et al. | |
| 2014/0257512 A1 | 9/2014 | Liu | |
| 2015/0230927 A1 * | 8/2015 | Lipman | A61F 2/3836 623/20.27 |
| 2015/0250597 A1 | 9/2015 | Lang et al. | |
| 2015/0335437 A1 | 11/2015 | Lauritzen et al. | |
| 2016/0113771 A1 | 4/2016 | McMinn | |
| 2016/0206375 A1 * | 7/2016 | Abbasi | A61B 34/30 |
| 2017/0086980 A1 | 3/2017 | Suckow | |
| 2018/0000598 A1 | 1/2018 | Amis et al. | |
| 2018/0325695 A1 | 11/2018 | Wozencroft | |
| 2019/0224367 A1 | 7/2019 | Kourtis et al. | |

FOREIGN PATENT DOCUMENTS

| | | |
|---|---|---|
| CN | 102276864 A | 12/2011 |
| CN | 202313810 U | 7/2012 |
| CN | 104042360 A | 9/2014 |
| CN | 203852451 U | 10/2014 |
| CN | 104887354 B | 9/2015 |
| CN | 204618485 U | 9/2015 |
| GB | 2139098 A | 7/1984 |
| GB | 2396561 A | 6/2004 |

OTHER PUBLICATIONS

Translated International Search Report issued to PCT Application No. PCT/CN2015/000664 dated Dec. 18, 2015.

* cited by examiner

COMBINED FULLY ORGANIC HIGH MOLECULAR MATERIAL ARTIFICIAL KNEE JOINT

TECHNICAL FIELD

The present invention relates to a medical rehabilitation instrument and, more particularly, to a combined fully organic high molecular material artificial knee joint.

BACKGROUND

Materials used for the implant are basically composed by Cobalt-Chrome-Molybdenum (Co—Cr—Mo) alloys and Ultra-high Molecular Weight Polyethylene (UHMWPE) since the total knee replacement is used in clinical treatment from the seventies of last century. The design of the knee prosthesis is mainly consisted of two interfaces, one of which is a fixed interface, and the other is a slide surface of the articular surface. The prosthesis is usually fixed by bone cement to the bone or by bony ingrowth directly to the bone, and the tibia component has been transformed from the polyethylene liner of the 1970s-to-1980s to the modular or combined liner used at present. Modern knee replacement requires doctors to know well of the soft tissue balance of the patients, and to adjust the thickness of the tibia liner in time during operation, so the modular tibia holder was widely used. The Co—Cr—Mo alloys are used in femur condyle and tibia holder, and the UHMWPE is used in friction surfaces of the tibia liner and the patella. Titanium (Ti) alloys have ever been used in the femur condyle and the tibia holder, but due to the friction surface between the Ti alloys and the UHMWPE is not ideal, the wear problem has not significantly improved even after a surface coating treatment, and therefore the Ti alloys femur condyle and the Ti alloys tibia holder are not widely used. In recent years, ceramic materials have been used to made femur condyles instead of Co—Cr—Mo alloys to reduce the wear of the UHMWPE. But because of their elastic modulus or stiffness is too high, and the impact resistance is relatively weak, the ceramic materials are limited to use in a small range (Bader R, Bergschmidt P, Fritsche A, Ansorge S, Thomas P, Mittelmeier W. (2008) Alternative materials and solutions in total knee arthroplasty for patients with metal allergy. Orthopade. 2008 February; 37 (2): 136-42). Since early this century, surface ceramic Zirconium-Niobium (Zr—Nb) alloys have been used for the femur condyle replacement. But because of their surface stiffness is still too high and the matrix is relatively softer, the wear problem is not completely solved (Essner A, Herrera L, Hughes P, Kester M. (2011) The influence of material and design on total knee replacement wear. J Knee Surg. 2011 March; 24 (1): 9-17), and the Zr—Nb alloys are too expensive, thus the Zr—Nb alloys are still limited to use in a small range. Therefore, in the history of artificial knee replacement for more than 50 years, the Co—Cr—Mo alloys and the UHMWPE are still the most common materials used for the implant.

Whether applied to the femur condyle or to the tibia holder, the metal or ceramic materials will cause some undesirable clinical problems. The first one is the wear problem of the UHMWPE slide surface (Kinney M C, Kamath A F. (2013) Osteolytic pseudotumor after cemented total knee arthroplasty. Am J Orthop (Belle Mead N.J.). 2013 November; 42(11): 512-4), and highly cross-linked UHMWPE widely used in the hip joint still can not be widely used in the knee joint (Hinarejos P, Piñol I, Torres A, Prats E, Gil-Gómez G, Puig-Verdie L. (2014) Highly cross-linked polyethylene does not reduce the wear in total knee arthroplasty: in vivo study of particles in synovial fluid. J Arthroplasty. 2013 September; 28(8): 1333-7). The second one is the wear problem of non-slide surface of the tibia holder caused by the fine movement between the metals and the UHMWPE (Banerjee S, Cherian J J, Bono J V, Kurtz S M, Geesink R, Meneghini R M, Delanois R E, Mont M A. (2014) Gross Trunnion Failure After Primary Total Hip Arthroplasty. J Arthroplasty. 2014 Nov. 26. pii: S0883-5403 (14) 00899-7). The third one is the stress shield problem between the metal or ceramic femur condyle and the natural bone (Panegrossi G, Ceretti M, Papalia M, Casella F, Favetti F, Falez F. (2014) Bone loss management in total knee revision surgery. Int Orthop. 2014 February; 38(2): 419-27). The fourth one is the stress shield problem between the metal tibia holder and the natural bone (Panegrossi G, Ceretti M, Papalia M, Casella F, Favetti F, Falez F. (2014) Bone loss management in total knee revision surgery. Int Orthop. 2014 February; 38(2): 419-27). The fifth one is anaphylaxis appeared in some patients and caused by a small amount of Nickel (Ni) contained in Co—Cr—Mo alloys (Innocenti M, Carulli C, Matassi F, Carossino A M, Brandi M L, Civinini R. (2014) Total knee arthroplasty in patients with hypersensitivity to metals. Int Orthop. 2014 February; 38(2): 329-33). The sixth one is that the metal materials have been inevitably corroded in the human body and thus release ions such as Co, Cr, Mo, Ni, and so on, and excessive metal ions release will produce toxicity to human (Kretzer J P, Reinders J, Sonntag R, Hagmann S, Streit M, Jeager S, Moradi B. (2014) Wear in total knee arthroplasty—just a question of polyethylene?: Metal ion release in total knee arthroplasty. Int Orthop. 2014 February; 38(2): 335-40). The seventh one is that metal materials, especially Co—Cr—Mo alloys, seriously affect magnetic resonance imaging (MRI) (Bachschmidt T J, Sutter R, Jakob P M, Pfirrmann C W, Nittka M. (2014) Knee implant imaging at 3 Tesla using high-bandwidth radiofrequency pulses. J Magn Reson Imaging. 2014 Aug. 23. doi: 10.1002/jmri.24729. [Epub ahead of print]).

For the design of the slide surface, British doctors and scientists had tried to use the total knee replacement fully formed by organic polymer materials in the clinical treatment as early as the 1990s (Plante-Bordeneuve P, Freeman M A. (1993) Tibia High-density polyethylene wear in conforming tibiofemoral prostheses J Bone Joint Surg Br. 1993 July; 75 (4): 630-6). The femur condyle is formed by Polyacetal (Delrin) polymer materials, the friction surface of the tibia is formed by UHMWPE, and the Polyacetal femur condyle is fixed to the natural bone by the bone cement or by compression without the bone cement, the UHMWPE friction component of the tibia is fixed to the natural bone by the bone cement. Ten years of clinical follow-up found that there is no unusual wear issue between the friction surfaces of the Polyacetal femur condyle and the UHMWPE, and the Polyacetal femur condyle has no mechanical damage issue too. However, Refurbishment is mainly caused by loose and early infection (Bradley G W, Freeman M A, Tuke M A, McKellop H A. (1993) Evaluation of wear in an all-polymer total knee replacement. Part 2: clinical evaluation of wear in a polyethylene on polyacetal total knee. Clin Mater. 1993; 14(2): 127-32: McKellop H A, Röstlund T, Bradley G. (1993) Evaluation of wear in an all-polymer total knee replacement. Part 1: laboratory testing of polyethylene on polyacetal bearing surfaces. Clin Mater. 14(2): 117-26: Moore D J, Freeman M A, Revell P A, Bradley G W, Tuke M. (1998) Can a total knee replacement prosthesis be made entirely of polymers? J Arthroplasty. 13(4): 388-95). Polyacetal used for the femur condyle was discontinued to use in clinical treatment as a result of poor chemical stability after γ-ray sterilization.

Therefore, so far the knee prostheses used in clinical treatment are all formed by metal materials, especially by Co—Cr—Mo alloys. The polymer materials above-mentioned have not been put into practical application as a result of a series of disadvantages.

In recent years, American scientists and researchers have found that due to the high-strength, high stability and good biological compatibility of polyether ether ketone (PEEK) polymer materials, the friction surface between the caput femoris formed by PEEK against the acetabular cup liner formed by UHMWPE exhibits a better wear resistance as compared with the case that the caput femoris is formed by PEEK, and the acetabular cup liner is formed by UHMWPE (Wang A G, Zhang Z T, Lawrynowicz D E and Yau S S (2010) Orthopedic PAEK-on-polymer bearings, HOWMEDICA OSTEONICS CORP, IPC8Class: AA61F230FI, USPC Class: 623-1811, Patent Application number: 20100312348, 2010-December 2009; Singh, V, Ogden, C, Sitton, K and Sitton, K (2012) Wear evaluation of different materials for total disc replacement (TDR), Proceedings of the ASME/STLE International Joint Tribology Conference, Los Angeles, Calif., 2011, 35-37, 2012).

Although the above studies have proposed the concept of the slide surface between PEEK and UHMWPE, the friction of the slide surfaces thereof is only suitable for articular surfaces with good matching degrees and low surface contact stress, such as ball-socket hip joint (wear extent: 16.5±1.8 mm$^3$/million, Wang A G, Zhang Z T, Lawrynowicz D E and Yau S S (2010) Orthopedic PAEK-on-polymer bearings, HOWMEDICA OSTEONICS CORP, IPC8 Class: AA61F230FI, USPC Class: 623-1811, Patent application number: 20100312348, 2010-December 2009). Moreover, the lower wear extent in the hip joint between PEEK and UHMWPE can not be directly reflected in the knee joint.

Due to different movement requirements, and impact suffered far greater than the hip joint, very complex surface shape of knee joint, and relatively poor matching degree, the pressure of knee joint surface (10~20 MPa) is much higher than the hip joint (2~5 MPa). These relatively harsh mechanical environments and the coupling with metal tibia holder which have a higher rigidity cause a significant increase of wear. The test according to ISO14243 shows that the wear between PEEK femur condyle and UHMWPE liner can reach 18.0±3.0 mm$^3$/million, which is higher than the wear of between Co—Cr—Mo femur condyle and UHMWPE liner used in present (9.0±4.0 mm<3>/Million, Fisher J, Jennings L M, Galvin A L, Jin Z M, Stone M H, Ingham E. (2010) Knee Society Presidential Guest Lecture: Polyethylene wear in total knees. Lt;/RTI > Epub 2009 Aug. 11), and this result further confirms that why the knee prostheses used in clinical treatment are all formed by metal materials (especially by Co—Cr—Mo alloys) till now.

In response to these problems, we have done a lot of experiments. The friction condition has improved by further treating the friction surface between the PEEK femur condyle and the UHMWPE liner, but still did not achieve the desired results. Whether in the metal tibia holder or the UHMWPE liner directly fixed on the tibia by bone cement, the above experiments have similar results.

Furthermore, we found that the wear of joint has a certain conduction and transfer under a high-intensity movement load according to the principle of tribology. It should be further optimized for the tibia holder to reduce the impact load, and to indirectly reduce the wear extent between the PEEK femur condyle and the UHMWPE liner. However, due to the structural characteristics of the knee joint, the tibia holder bears the most loads. It has never been mentioned that tibia holder can use other materials, whether in the clinical practices or in the literatures. Thus, the key point of the present invention is whether or not the alternative materials can be found to meet the requirement of strength, and meanwhile to meet the operating requirements of reducing the impact load and the wear. These alternative materials should make the artificial knee system overall superior to the artificial knee fully formed by metal materials, in particular Co—Cr—Mo alloys.

SUMMARY

The present invention first proposes an artificial knee joint system formed by polymer, comprising a femur condyle, a tibia liner and a tibia holder, wherein the femur condyle and the tibia holder are formed by polyether ether ketone (PEEK) or derivatives thereof, and the tibia liner is formed by ultra-high molecular weight polyethylene (UHMWPE). Because of the creative use of the tibia holder formed by PEEK or derivatives thereof (also referred to as "PEEK tibia holder"), the knee joint structure of the present invention makes it possible that the femur condyle formed by PEEK is used together with the tibia liner formed by ultra-high molecular weight polyethylene in the knee joint system. In the present invention, the matching of material properties between the UHMWPE tibia liner and the PEEK tibia holder may increase the buffering of the PEEK femur condyle against the slide surface of the UHMWPE tibia liner, and may control the fine movement between the PEEK femur condyle and the slide surface of the UHMWPE tibia liner, so as to affect the wear mechanism between the PEEK femur condyle and the UHMWPE tibia liner. Moreover, the PEEK tibia holder is able to transmit the movement load effectively, so that buffering of the PEEK femur condyle against the slide surface of the UHMWPE tibia liner matches the fine movement of the PEEK tibia holder relative to the UHMWPE tibia liner, and thus the alternating shear caused by the multi-directional movement is reduced, and the overall wear of the two surfaces of the polyethylene liner may greatly be reduced. The test according to ISO14243 shows that the wear extent is reduced to 5.0±1.2 mm$^3$/million, which is significantly better than the wear extent (9.0±4.0 mm$^3$/million) of prior art in which the femur condyle and the tibia holder are formed by Co—Cr—Mo alloys and the tibia liner is formed by UHMWPE. Therefore, it can be predicted that the knee joint based on wear can prolong its life from the current 20 years to 40 years. This fully provides a possibility that the total knee joint system based on PEEK is used in clinical treatment.

In addition, because the clinical problems caused by the use of metallic materials, such as the sensitivity to metal ions, toxicity from metal ions, pseudotumor caused by metal ions, and the like, are reduced, and because the elastic modulus of the PEEK materials (the elastic modulus is 3 GPa) is far less than that of metals (the elastic modulus is 200 GPa), but approximates that of a bone (the elastic modulus is 0.8~17 GPa), PEEK tibia holder used in the present invention can reduce stress shield of the tibia to avoid it absorbed by bone, and thus make a good fixed effect for more than 30 years. These advantages will enable the knee system fully formed by polymer to be widely used in different patients, especially young patients. Because of there are no needs for clinical renovations in using of the knee joint system according to the present invention, it may not only reduce the patient's pain, but also may greatly reduce medical cost. In addition, the present invention further solves clamping problem of polymer components in surgical procedure so as not to damage the polymer prosthesis, and so solves the practical problems of polymer prosthesis used in clinical treatment. Meanwhile, the present invention also solves developing problem of the polymer prosthesis after surgery, so as to observe the operation result and the long-term service of the prosthesis in human body.

In order to realize the above-mentioned object of the invention, a technical solution provided by the present invention is: a combined fully organic high molecular material artificial knee joint comprising a femur condyle, a tibia liner and a tibia holder, wherein:

the tibia holder comprises a platform and a stable wing positioning portion vertical thereto; the femur condyle is jointed to an upper end of the tibia liner and the platform of the tibia holder is jointed to a lower end of the tibia liner; the femur condyle, the tibia holder and the tibia liner are all formed by the high molecular material, wherein the femur condyle and the tibia holder being formed by polyether ether ketone or derivatives thereof, and the tibia liner being formed by ultra-high molecular weight polyethylene; the femur condyle buffers a slide surface of the tibia liner, the tibia holder can finely move relative to a fixed surface of the tibia liner, and buffering of the femur condyle against the slide surface of the tibia liner matches fine movement of the tibia holder relative to the fixed surface of the tibia liner.

Further, the combined fully organic high molecular material artificial knee joint further comprising a patella, wherein the patella is formed by ultra-high molecular weight polyethylene, and the patella is jointed to an upper end of the femur condyle.

Further, X-ray developing additives are contained in the femur condyle and in the tibia holder.

Further, each of the left side and right side of the femur condyle is provided with a groove; and a metal or ceramic inlay matching the shape of the groove is included in the groove.

Further, one or more metal strip parts is provided on a side of the upper end of the platform of the tibia holder.

Further, a metal reinforcing component is provided at an interface between outer end of the stable wing positioning portion and the platform of the tibia holder; and a metal reinforcing column perpendicular to the platform of the tibia holder is provided in the center of the stable wing positioning portion.

Further, the height and thickness of the metal strip parts both are not less than 0.5 mm and not more than 3.0 mm.

Further, the diameter of the metal reinforcing column is not less than 1.0 mm and not more than 10 mm.

Further, the metal inlays, the metal reinforcing component, the metal reinforcing column, and the metal strip parts are all formed by biocompatible metals or alloys thereof.

Further, the metals or alloys thereof include Co—Cr—Mo alloys, Ti or Ti alloys, Ta or Ta alloys, stainless steels and/or Zr—Nb alloys.

Employing above-mentioned technical solution, the beneficial effects of the present invention are:

1. The main parts of all implant components for artificial knee joint provided by the present invention are formed by molecular materials, thereby relieving allergy and toxicity problems caused by metal and metal corrosion.

2. The elastic modulus of PEEK according to the present invention matches that of a natural bone, thereby relieving a stress shield problem.

3. The wearing problem is relieved by means of the combination of buffering of the PEEK femur condyle against the slide surface of the UHMWPE tibia liner and fine movement of the tibia holder relative to the fixed surface of the UHMWPE tibia liner according to the present invention.

4. All the implant formed by molecular materials in the present invention do not interfere magnetic resonance imaging.

DETAILED DESCRIPTION

In order to make the objects, technical solutions and advantages of the present disclosure more clearly understood, the present disclosure will be described in further detail with reference to the accompanying drawings and embodiments below. It should be understood that the specific embodiments described herein are only used to explain the present disclosure and are not intended to limit the present disclosure.

Figure 1:
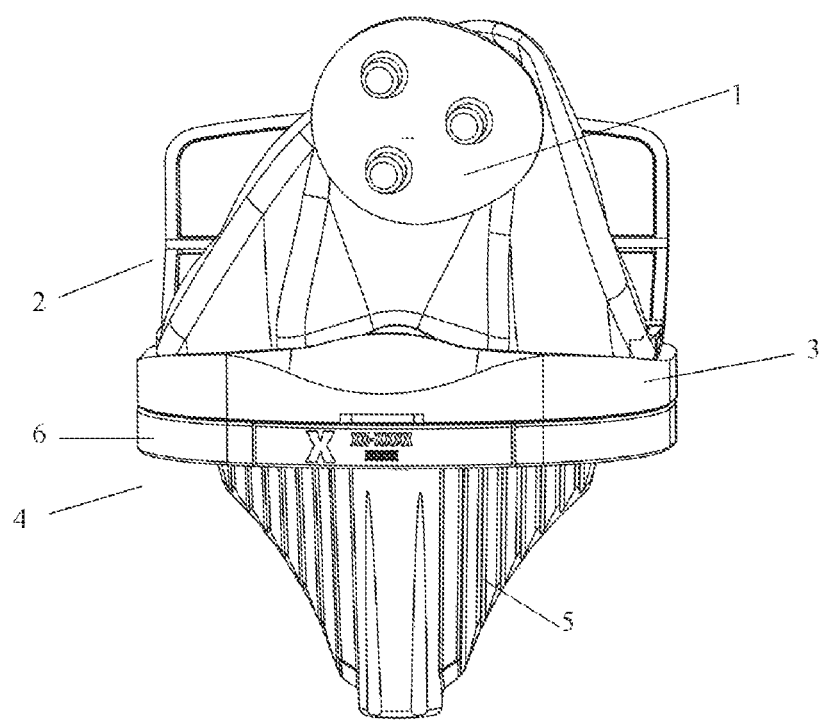
FIG. 1 is a structural schematic diagram of a combined fully organic high molecular material artificial knee joint provided by the present invention.
Figure 3:
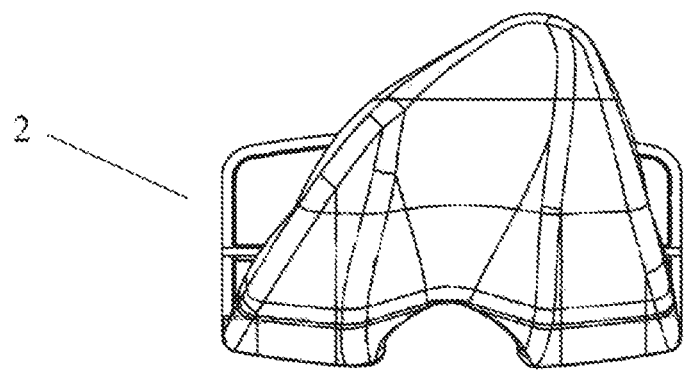
FIG. 3 is a structural schematic diagram of a femur condyle in the present invention.
Figure 6:
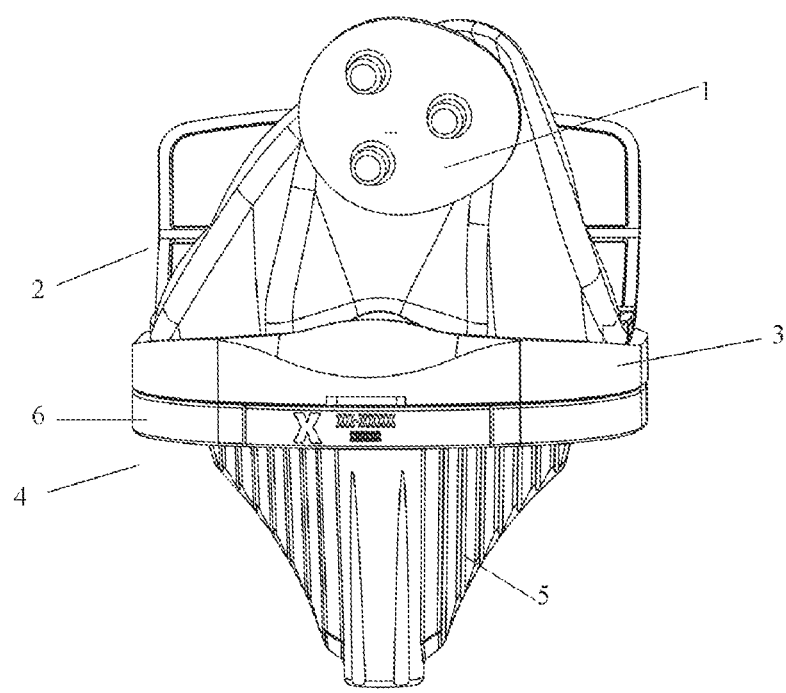
FIG. 6 is a structural schematic diagram of a tibia holder in the structure of FIG. 1 of the present invention, the lower end of which is embedded with metal reinforcing column.

As shown in FIGS. 1, 3 and 6, the present invention provides a combined fully organic high molecular material artificial knee joint comprising a femur condyle 2, a tibia liner 3, a tibia holder 4 and a patella 1, wherein the tibia holder 4 comprises a platform 6 and a stable wing positioning portion 5 with a section, and the stable wing positioning portion 5 is positioned below the platform 6 of the tibia holder 4 and perpendiculars to the platform 6. The stable wing positioning portion 5 is used to make the tibia holder 4 fixed on the human skeleton, and so as to fix the whole artificial modular knee joint on the human skeleton. The patella 1 is jointed to an upper end of the femur condyle 2, a lower end of the femur condyle 2 is jointed to an upper end of the tibia liner 3, and the platform 6 is jointed to a lower end of the tibia liner 3. Each of the femur condyle 2, the tibia liner 3, the tibia holder 4 and the patella 1 is formed by polymer materials, wherein the femur condyle 2 and the tibia holder 4 both are formed by polyether ether ketone (PEEK) or derivatives thereof and the tibia liner 3 and the patella 1 are formed by ultra-high molecular weight polyethylene (UHMWPE).

Moreover, in the present invention, the femur condyle 2 may buffer a slide surface of the tibia liner 3, and the tibia holder 4 may finely move relative to a fixed surface of the tibia liner 3. The buffering of the slide surface may control the fine displacement between the tibia holder 4 and the tibia liner 3, and because of the PEEK tibia holder 4 is able to transmit the movement load effectively, so that buffering of the femur condyle 2 against the slide surface of the tibia liner 3 matches fine movement of the tibia holder 4 relative to the fixed surface of the tibia liner 3, and then the alternating shear caused by the multi-directional movement is reduced, and the overall wear of the two surfaces of the UHMWPE tibia liner 3 may greatly be reduced.

The test according to ISO14243 shows that the wear extent of the two surfaces of the UHMWPE tibia liner 3 according to the above technical solution is reduced to 5.0±1.2 mm$^3$/million, which is significantly better than the wear extent (9.0±4.0 mm$^3$/million) of the two surfaces of the Co—Cr—Mo alloys against UHMWPE used in present. Therefore, it can be predicted that the knee joint based on wear can prolong its life from the current 20 years to 40 years. This fully provides a possibility that the total knee joint system based on PEEK is used in clinical treatment.

In addition, because the clinical problems caused by the use of metallic materials, such as the sensitivity to metal ions, toxicity from metal ions, pseudotumor caused by metal ions, and the like, is reduced, and because the elastic modulus of the PEEK materials (the elastic modulus is 3 GPa) is far less than that of the metals (the elastic modulus is 200 GPa), but approximates that of the bone (the elastic modulus is 0.8~17 GPa), the PEEK tibia holder 4 according to the above technical solution can reduce stress shield of the tibia to avoid it absorbed by bone, and thus make a good fixed effect for more than 30 years. These advantages will enable the knee system fully formed by polymer to be widely used in different patients, especially young patients. Because of there are no needs for clinical renovations in using of the knee joint system according to the present invention, it may not only reduce the patient's pain, but also may greatly reduce medical cost.

Figure 2:
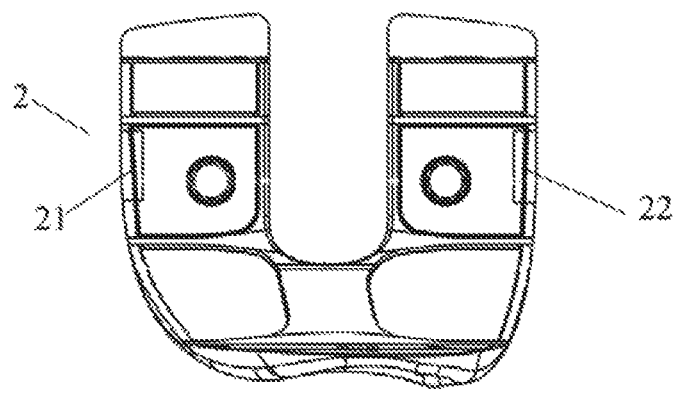
FIG. 2 is a top view of a femur condyle in the present invention showing a structural schematic diagram of the femur condyle with metal inlay on both sides thereof.

In addition, in the above technical solution, the PEEK femur condyle 2 of the present invention can solve two potential clinical use problems by further optimal design. One is X-ray imaging problem of the PEEK femur condyle 2, and the other is the joint problem between the surgical clips and the PEEK femur condyle 2 during the surgical procedure. In the clinical treatment and postoperative, X-ray imaging problem of an implant formed by high molecular materials is solved by inlaying beads formed by Ta or alloys thereof into relevant portions. In the present invention, the joint between the surgical clips and the femur condyle 2 is implemented by grooves provided in the left and right sides of the femur condyle 2. However, due to hardness and strength of the PEEK are much lower than that of the surgical clips formed by metal material (the surgical clips are generally formed by stainless steel), the groove wall formed by the PEEK has a risk of damage during surgery. In order to solve the X-ray imaging problem and to prevent the risk of the PEEK femoral groove wall damaged during surgery, the above-mentioned technical solution further comprises the following structure: metal inlays 21 and 22 are inlaid on the grooves provided in the left and right sides of the femur condyle 2 as shown in FIG. 2. The thickness of the metal inlays 21 and 22 is not less than 0.5 mm and not more than 3.0 mm, and the metal inlays 21 and 22 are formed by a biocompatible metals or alloys thereof such as Co—Cr—Mo alloys, Ti or Ti alloys, Ta or Ta alloys, stainless steels, Zr—Nb alloys and so on. Based on the above-mentioned structure, the metal inlays 21 and 22 inlaid in the PEEK femur condyle 2 will have dual effect of implementing X-ray development of femur condyle 2 and preventing the femur condyle 2 from potential damage caused by the surgical clips.

Figure 4:
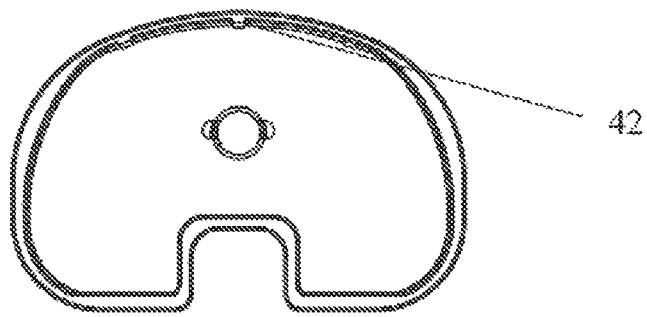
FIG. 4 is a structural schematic diagram of a platform of a tibia holder according to the present invention, the side of the upper end of which embedded with metal strip parts.
Figure 5:
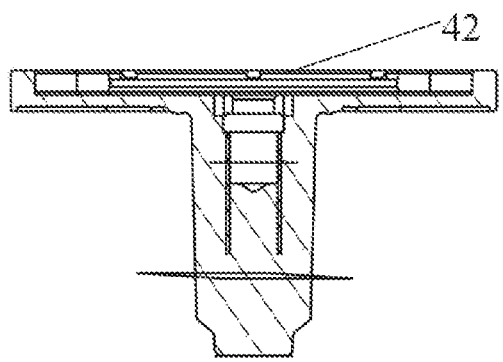
FIG. 5 is a cross-section view of the structure of FIG. 4 of the present invention.

In the above technical solution, the PEEK tibia holder 4 of the present invention can also solve two potential problems by further optimal design. One is X-ray imaging problem of the PEEK tibia holder 4, and the other is the fixing problem between the PEEK tibia holder 4 and the UHMWPE tibia liner 3. In the present invention, one or more metal strip parts 42 is inlaid in the side, particularly in the front side, of the platform 6 of the PEEK tibia holder 4 as shown in FIGS. 4 and 5 (metal strip parts 42 are inlaid in the side of the platform 6 which is connected with tibia liner 3 during operation). The height and the thickness/diameter of the metal strip parts 42 both are preferably not less than 0.5 mm and not more than 3.0 mm, and the metal strip parts 42 are formed by a biocompatible metals or alloys thereof: such as Co—Cr—Mo alloys, Ti or Ti alloys, Ta or Ta alloys, stainless steels, Zr—Nb alloys and so on. Based on the above-mentioned structure, the PEEK tibia holder 4 with metal part inlaid in its side will have dual effect of implementing X-ray development of tibia holder 4 and reinforcing the connection between the PEEK tibia holder 4 and the UHMWPE tibia liner 3.

Furthermore, in the above technical solution, a metal reinforcing component (not shown) is provided at an interface between outer end of the stable wing positioning portion 5 and the platform 6 of the tibia holder 4, and a metal reinforcing column 41 which perpendiculars to the platform 6 of the tibia holder 4 is provided in the center of the stable wing positioning portion 5 as shown in FIG. 6. The diameter of the metal reinforcing column 41 is preferably not less than 1.0 mm and not more than 10 mm, and the metal reinforcing column 41 is formed by a biocompatible metals or alloys thereof, such as Co—Cr—Mo alloys, Ti or Ti alloys, Ta or Ta alloys, stainless steels, Zr—Nb alloys and so on. Based on the above-mentioned structure, the PEEK tibia holder 4 with a metal reinforcing column 41 will have dual effect of implementing X-ray development of tibia holder 4 and enhancing the load (includes an impact during operation and a motion force after surgery) capacity of the stable wing positioning portion 5.

Thus, the present invention further solves clamping problem of polymer components in surgical procedure so as not to damage the polymer prosthesis, and solves the practical problems of polymer prosthesis used in clinical treatment. Meanwhile, the present invention also solves developing problem of the polymer prosthesis after surgery, so that observe the operation result and the long-term service of the prosthesis in the human body.

The above descriptions are only preferred embodiments of the present disclosure and are not intended to limit the implementation scope of the present disclosure. Modifications or equivalent substitutions of the present disclosure should be covered by the protective scope of the claims of the present disclosure without departing from the spirit and scope of the disclosure.

LIST OF REFERENCE SIGNS 1 patella
2 femur condyle
3 tibia liner
4 tibia holder
5 stable wing positioning portion
6 platform
21 metal inlay
22 metal inlay
41 metal reinforcing column
42 metal strip part.

What is claimed is:

1. A combined fully organic high molecular material artificial knee joint comprising:
   a femur condyle;
   a tibia liner;
   a tibia holder;
   wherein the tibia holder comprises a platform and a stable wing positioning portion vertical thereto;
   wherein the femur condyle is jointed to an upper end of the tibia liner and the platform of the tibia holder is jointed to a lower end of the tibia liner;
   wherein the femur condyle, the tibia holder and the tibia liner are all formed by a high molecular material;
   wherein the tibia liner is formed by ultra-high molecular weight polyethylene (UHMWPE); and
   wherein each of a left side and a right side of the femur condyle is provided with a groove, and wherein a metal or ceramic inlay matching the shape of the groove is included in the groove.

2. The combined fully organic high molecular material artificial knee joint of claim 1, wherein the femur condyle and the tibia holder are formed by polyether ether ketone or derivatives thereof.

3. The combined fully organic high molecular material artificial knee joint of claim 1, wherein the tibia liner is formed by ultra-high molecular weight polyethylene.

4. The combined fully organic high molecular material artificial knee joint of claim 1, further comprising a patella, wherein the patella is formed by ultra-high molecular weight polyethylene, and the patella is jointed to an upper end of the femur condyle.

5. The combined fully organic high molecular material artificial knee joint of claim 1, wherein X-ray developing additives are contained in the femur condyle and in the tibia holder.

6. The combined fully organic high molecular material artificial knee joint of claim 1, wherein the metals or alloys thereof include Co—Cr—Mo alloys, Ti or Ti alloys, Ta or Ta alloys, stainless steels, and/or Zr—Nb alloys.

7. The combined fully organic high molecular material artificial knee joint of claim 1, wherein one or more metal strip parts is provided on a side of the upper end of the platform of the tibia holder.

8. The combined fully organic high molecular material artificial knee joint of claim 1, wherein the height and thickness of the metal strip parts are not less than 0.5 mm and not more than 3.0 mm.

9. The combined fully organic high molecular material artificial knee joint of claim 1, wherein the metals or alloys thereof include Co—Cr—Mo alloys, Ti or Ti alloys, Ta or Ta alloys, stainless steels, and/or Zr—Nb alloys.

10. The combined fully organic high molecular material artificial knee joint of claim 1, wherein a metal reinforcing component is provided at an interface between outer end of the stable wing positioning portion and the platform of the tibia holder; and a metal reinforcing column perpendicular to the platform of the tibia holder is provided in the center of the stable wing positioning portion.

11. The combined fully organic high molecular material artificial knee joint of claim 10, wherein the diameter of the metal reinforcing column is not less than 1.0 mm and not more than 10 mm.

12. The combined fully organic high molecular material artificial knee joint of claim 10, wherein the metal inlays, the metal reinforcing component, the metal reinforcing column, and the metal strip parts are all formed by biocompatible metals or alloys thereof.

13. The combined fully organic high molecular material artificial knee joint of claim 1, wherein the metals or alloys thereof include Co—Cr—Mo alloys, Ti or Ti alloys, Ta or Ta alloys, stainless steels, and/or Zr—Nb alloys.

14. A combined fully organic high molecular material artificial knee joint comprising:
   a femur condyle;
   a tibia liner;
   a tibia holder;
   wherein the tibia holder comprises a platform and a stable wing positioning portion vertical thereto;
   wherein the femur condyle is jointed to an upper end of the tibia liner and the platform of the tibia holder is jointed to a lower end of the tibia liner;
   wherein the femur condyle, the tibia holder and the tibia liner are all formed using a high molecular material, the femur condyle and the tibia holder are formed with polyether ether ketone (PEEK) or derivatives thereof, and the tibia liner is formed with ultra-high molecular weight polyethylene (UHMWPE); and
   wherein each of a left side and a right side of the femur condyle is provided with a groove, and wherein a metal or ceramic inlay matching the shape of the groove is included in the groove.

* * * * *